United States Patent [19]

Rounds

[11] Patent Number: 5,663,285
[45] Date of Patent: Sep. 2, 1997

[54] BLOOD COMPATIBLE, SHEAR SENSITIVE FORMULATIONS

[75] Inventor: Rhyta S. Rounds, Flemington, N.J.

[73] Assignee: Becton Dickinson and Company, Franklin Lakes, N.J.

[21] Appl. No.: 699,141

[22] Filed: Aug. 16, 1996

Related U.S. Application Data

[63] Continuation of Ser. No. 318,586, Oct. 5, 1994, abandoned.
[51] Int. Cl.$^6$ .................................................. C08G 69/38
[52] U.S. Cl. ................ 528/320; 528/396; 528/483; 524/5; 524/474; 524/492; 524/497; 524/588
[58] Field of Search ..................... 528/320, 396, 528/483; 524/5, 474, 492, 497, 588; 424/11

[56] References Cited

U.S. PATENT DOCUMENTS

| | | |
|---|---|---|
| 4,148,764 | 4/1979 | Lamont et al. |
| 4,994,393 | 2/1991 | Pradhan et al. |
| 5,124,434 | 6/1992 | O'Brien |
| 5,310,540 | 5/1994 | Giddey et al. ......................... 424/9 |

OTHER PUBLICATIONS

A presentation given by Philip B. Mendershausen, Ph.D., on the subject of Barrier Gel Adhesion to Sampling Probes, Presented on Tuesday, Jul. 13, 1993 at the 45th National Meeting of the American Association for Clinical Chemistry in New York City, New York.

*Primary Examiner*—Nathan M. Nutter
*Assistant Examiner*—Duc Truong
*Attorney, Agent, or Firm*—Nanette S. Thomas

[57] ABSTRACT

Formulations including a high density polyester and a density reducing component. The formulations are useful for facilitating the separation of blood serum or plasma from the cellular portion of blood in blood collection applications.

1 Claim, 8 Drawing Sheets

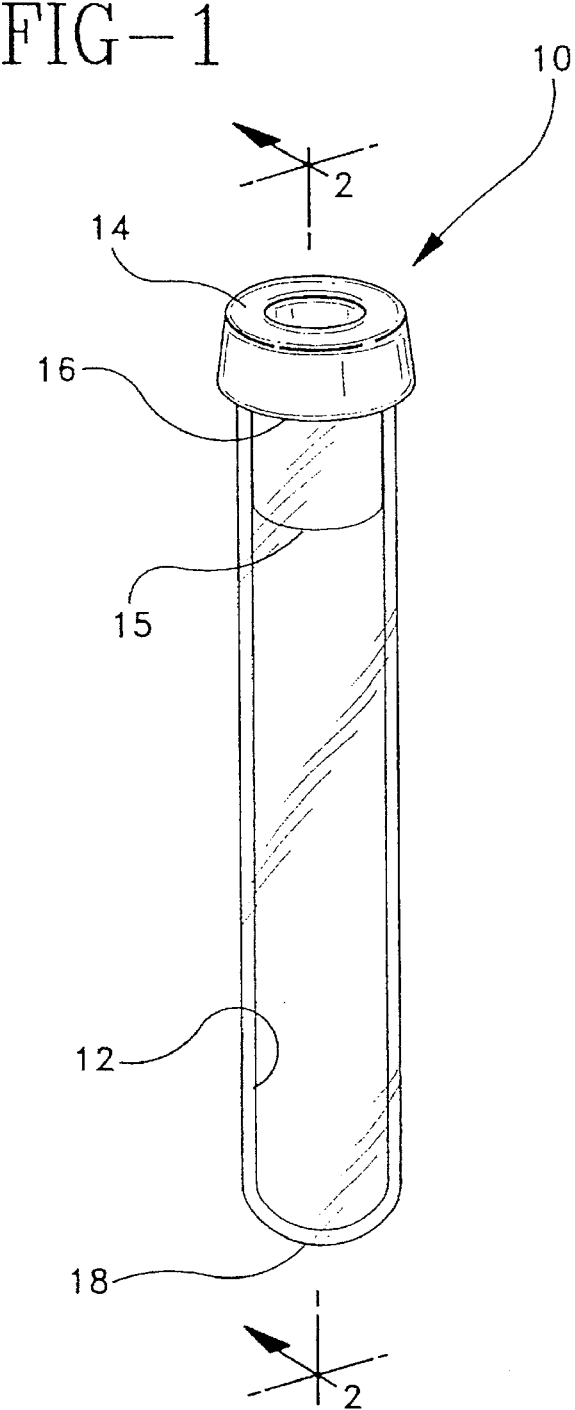
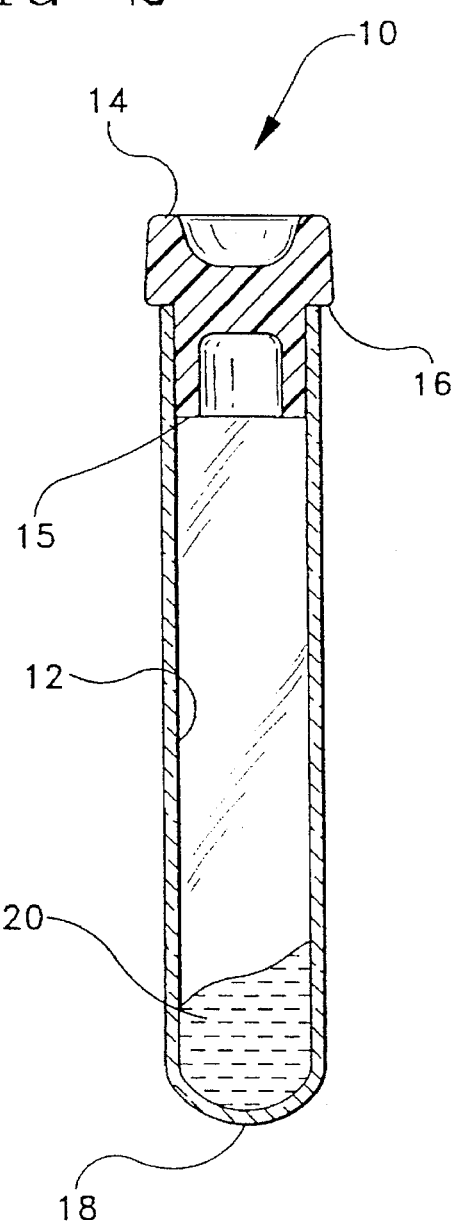

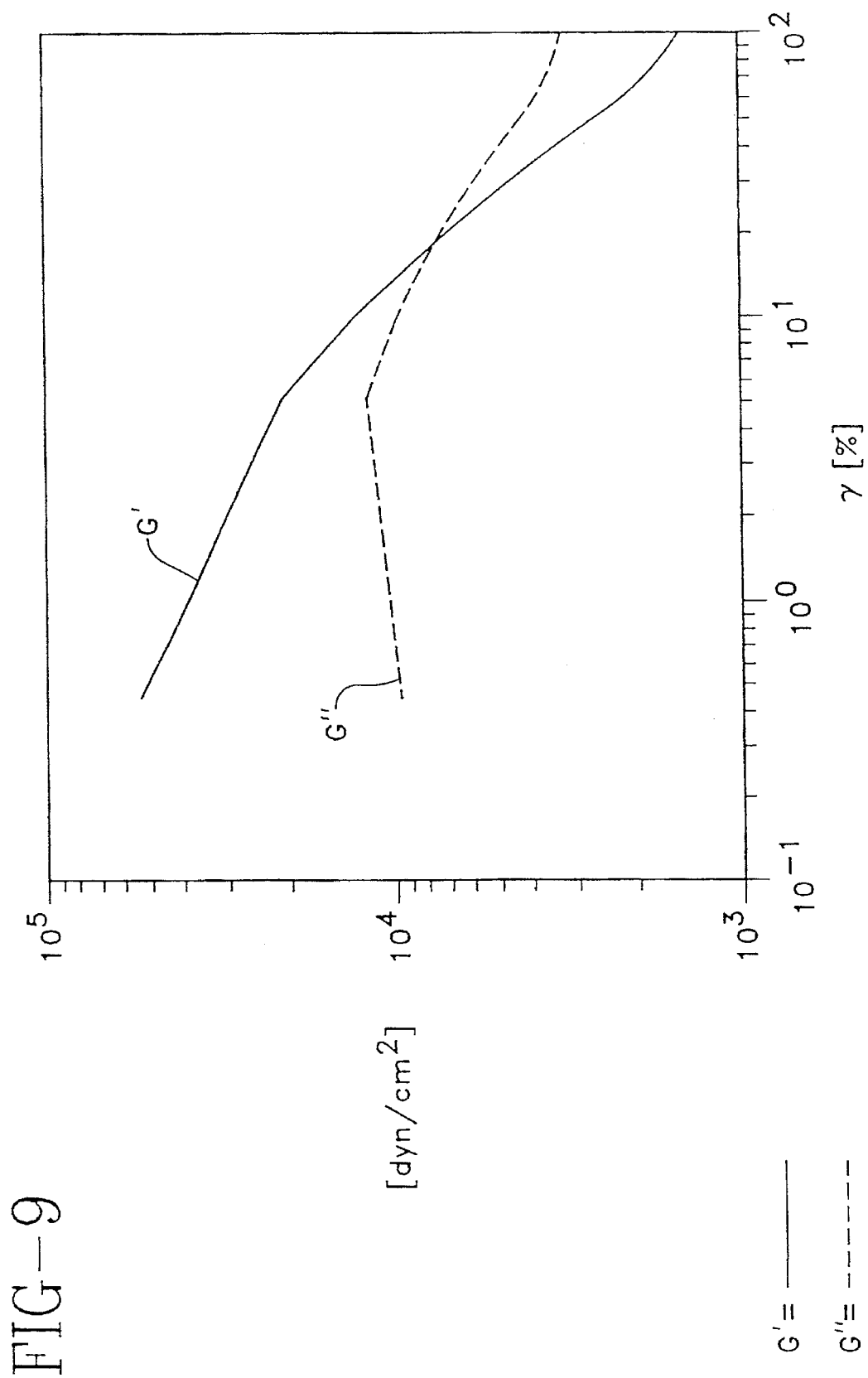

BLOOD COMPATIBLE, SHEAR SENSITIVE FORMULATIONS

This is a continuation of application Ser. No. 08/318,586, filed on Oct. 5, 1994, now abandoned.

BACKGROUND OF THE INVENTION

1. Field of the Invention

This invention relates to formulations that are blood compatible and shear sensitive. More particularly, such formulations comprising a high density, polymer in combination with a density reducing component are particularly useful for facilitating the separation of blood serum or plasma from the cellular portion of blood.

2. Description of the Related Art

Biochemical tests carded out in a clinical laboratory require use of blood serum or plasma as a sample. For preparing the sample for examination, it is frequently necessary to separate the blood serum or plasma from the solid blood components. There are various types of blood separating compositions which are used to separate the blood components from one another. In particular, serum separators are dispersions consisting of hydrophobic polymers and additives to regulate density and rheology. Typical separators contain low density polymers such as polyesters with silica thickeners which increase the density and form the required flow properties. The main ingredient in such compositions, is a polymer.

U.S. Pat. Nos. 3,780,935, 3,920,549, 3,997,442 and 4,148,764 for example, disclose polyester compositions that exhibit thixotropic like properties. In particular, U.S. Pat. No. 5,124,434 discloses a composition that also exhibits thixotropic properties comprising a polyester with a density of 1.01 to 1.09, comprising one mole of a dicarboxylic acid member and one mole of a diol member wherein said acid member is comprised of a first dicarboxylic acid component having from about 5 to about 60 mole percent of an aliphatic dicarboxylic acid having from 13 to about 22 carbon atoms, a second dicarboxylic acid component having from about 35 to about 90 mole percent of an aliphatic dicarboxylic acid having from 4 to about 12 carbon atoms, a third dicarboxylic acid component having from about 5 to about 25 mole percent of an aliphatic dicarboxylic acid having about 36 carbon atoms.

Whereas there are numerous publications related to compositions useful for facilitating the separation of blood serum of plasma from the cellular portion of blood, there are no publications that suggest or teach polymers with a high density combined with a density reducing component to yield blood compatible and shear sensitive gel formulations.

SUMMARY OF THE INVENTION

The present invention is serum/plasma separator formulations for use in blood collection tubes, comprising (a) a high density polyester and (b) a density reducing component.

Desirably, the serum/plasma separator formulations of the present invention may further comprise silica, titanium dioxide, a physical cross-linking agent and/or a stabilizing agent.

Preferably, the serum/plasma separator formulations of the present invention have a density from about 1.02 to about 1.06 and most preferably at about 1.04 at 25° C.

Preferably, the serum/plasma separator formulations of the present invention have a viscosity of from about $0.6 \times 10^3$ to about $3.2 \times 10^3$ Pascal seconds; preferably from about $2.3 \times 10^3$ to about $3.2 \times 10^3$ Pascal seconds and most preferably at about an average of $2.7 \times 10^3$ Pascal seconds, at a shear rate of 0.05 $sec^{-1}$ at 300 seconds.

Preferably, the serum/plasma separator formulations of the present invention are viscoelastic having a storage modulus, G' of about $5.3 \times 10^3$ to about $2.2 \times 10^3$ Pascals at a strain of about 0.005 and frequency of 10 radians/sec and most preferably at about $3.7 \times 10^3$ Pascals.

The polyester in the serum/plasma separator formulations preferably have a low molecular weight and a hydroxy terminated or alkyl termination with low a degree of functionality.

Most preferably, the polyester is liquid at room temperature, hydrophobic, stable and nonionic.

Polyesters generally exhibit a broad distribution of physical and chemical properties including molecular weight distribution and density. It is known that serum and plasma can be contaminated with gel fragments following centrifugation of donor specimen. Therefore, a desirable characteristic of the serum/plasma separator formulations of the present invention is the use of a higher density polyester component to minimize the occurrence of polyester segments in the separated blood components. Most preferably, the serum/plasma separator of the present invention comprise a high density polymer such as an adipate polyester and incorporates a specific component to reduce the density of the formulation achieving the needed specific gravity for blood serum/plasma separation.

Preferably, the density reducing component of the formulations of the present invention are hollow microspheres, low density polymers/copolymers or air. Most preferably the density reducing component is hollow microspheres.

Preferably, hollow microspheres are in the formulations of the present invention from about 0.2% to about 15% by weight and most preferably at about 6%.

Alternatively, the density reducing component may desirably be a mineral oil gel comprising a di-block and tri-block copolymer.

The co-polymer gel may be in the formulations of the present invention from about 20% to about 50% and most preferably at about 49%. Preferably, silica may be added to the formulations of the present invention for rheology and/or density modification of the formulations.

Preferably, titanium dioxide may be added to the formulations of present invention to render the formulations opaque.

Preferably, a low concentration, high molecular weight rheology modifier, such as a liquid polyoxyalkylene polyol may be added to the formulations of the present invention because the polyol such as trimethylalpropane based polyol, having a molecular weight of about 22,000, may substantially thicken the formulation. The polyol preferably has a specific gravity of about 1.085 to about 1.095 at about 25° C. and exhibits a viscosity of about 6000 centi-strokes at about 210° F.

The gel formulations of the present invention are particularly useful for facilitating the separation of blood serum or plasma from the cellular portion of blood when used in blood collection tubes.

Attributes of the serum/plasma separator formulations of the present inventions include: thermoversibility properties in that the separator can be heated to a viscous liquid state that returns to gel on cooling, retaining a substantially clear appearance and the ability to flow under shear forces involved in centrifugation. Consequently, serum/plasma separator formulations of the present invention do not irreversibly liquefy under certain shear forces and exhibit thixotropic-like behavior and therefore are useful as serum separation gels in blood collection applications.

Another advantage of the serum/plasma separator formulations of the present invention is its ability to maintain uniform physical and chemical properties for extended periods of time prior to use, as well as during transportation and processing of blood samples. Therefore, the components of the serum/plasma separator formulations of the present invention will not separate under normal storage and/or use. Furthermore, the serum/plasma separator formulations of the present invention are hydrophobic, inert, nonionic, and relatively impermeable.

Most notably, the gel formulations of the present invention readily form a stable portion under normal centrifugation conditions and are relatively inert or unreactive toward the substances in the blood whose presence or concentration is to be determined. Therefore, the serum/plasma separator formulations of the present invention are blood compatible and can be readily used in blood collection applications. As compared to hydrocarbon silicone type oils that are typically used in blood collection applications, the serum/plasma separator formulations of the present invention will not attract cells and clot debris that is in blood specimens.

The serum/plasma separator formulations of the present invention also are thixotropic or exhibit thixotropic—like properties in that these formulations will flow under stress imposed during centrifugation of blood. When used in a blood collection tube the serum/plasma separator formulation reforms into a solid barrier that mechanically separates solid and liquid blood components on the basis of density when centrifugation is ceased. Since deformation of a solid barrier is essential to blood separation that resists inadvertent mechanical remixing as might occur during transport or storage of blood specimens the serum/plasma separator formulations of the present invention are acceptable for use in blood collection applications.

Furthermore, a desirable characteristic of the serum/plasma separator formulations of the present invention is that it is not restricted to low density polymers. In particular, a desirable characteristic of the serum/plasma separator formulations of the present invention is that high density polyesters are used in the formulation and density modification achieved with low density hollow microspheres for the purpose of achieving higher purity specimen separation while maintaining the needed rheological properties.

Another advantage of the polymer blends of the present invention is that they are formed of all synthetic materials and therefore raw material variability is reduced.

The surprising characteristic of the formulations of the present invention is that separators can be achieved with significant elastic effects, showing true gel behavior as characterized by chemically cross-linked polymers. In particular, the formulations of the present invention exhibit linear viscoelastic properties, capable of withstanding forces without flow and more solid-like behavior. Most notably is the stability of the formulations of the present invention as compared to the formulations used in commercially available serum separator products that are non-linear dispersions which exhibit poor stability and lack well defined yield stress.

DESCRIPTION OF THE DRAWINGS

FIG. 1 is a perspective view of a typical blood collection tube with a stopper.

FIG. 2 is a longitudinal sectional view of the tube of FIG. 1, taken along line 2—2, comprising a gel formulation of the present invention.

FIGS. 3–10 illustrate the dynamic mechanical measurements, strain dependence of the storage modules, G', and the loss modulus, G", at a frequency of 10 rads/sec, of each sample in Table 1.

DETAILED DESCRIPTION

Figure 3:
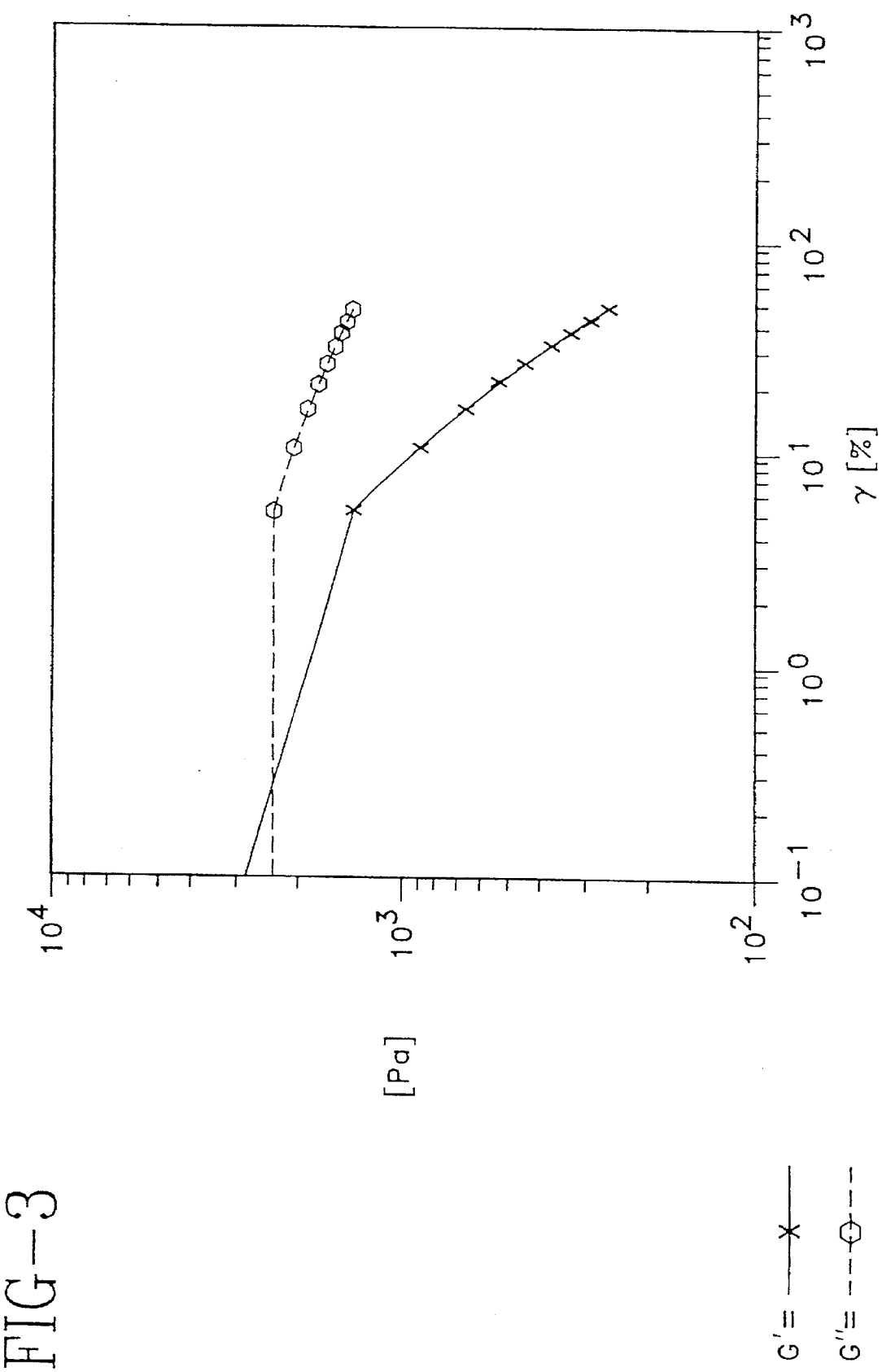

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The serum/plasma separator formulations of the present invention preferably comprise a high density polyester and a density reducing component so as to reduce the density of the polyester.

Preferably, the serum/plasma separator formulations of the present invention have a viscosity at 0.05 $sec^{-1}$ from about 2300 Pascals seconds to about 3200 Pascals seconds and a density from about 1.02 to about 1.05. Most preferably, the formulations have a viscosity of about 2700 Pascals seconds and a density of about 1.04.

Preferably, the serum/plasma separator formulations of the present invention are non-linear viscoelastic dispersions or gels.

Most preferably, the high density polyester of the present invention are polyols, a linear or branched adipate with hydroxy termination although alkyl termination maybe preferable, making the polyester more inert.

Most preferably, the polyesters are liquid polymers at room temperature, hydrophobic, stable and nonionic.

Most notably, commercially available polyester resins are synthesized from adipic acid, resulting in resins with a specific gravity of greater than 1.08 and having a low molecular weight. These low molecular weight resins cannot be used to formulate serum separator barriers without modification since the required specific gravity required for a serum separation barrier is approximately 1.04. Therefore, the present invention recognizes the need to form polymer blends or dispersions using lower density hydrocarbon polymers or light density solid phase polymers or air.

Most preferably, the polyols are useful in the formulations of the present invention include, but are not limited to linear adipate diols, branched adipates and branched adipate isophthalate diols, having a viscosity (cps) of about 23,000 to about 8,000 cps at about 25° C.

The high density polyester is preferably present in the formulations of the present invention from about 85% to about 97% by weight and preferably at about 94% by weight.

Most preferably, the density reducing component of the present invention is a low density component, such as oleophilic hollow microspheres. Most preferably, the hollow microspheres are single-cell white spheres that are free flowing, have a hydrophobic coating and an effective density of about 0.28 to about 0.10 (g/cm$^3$)

Hollow microspheres are preferably present in the formulations of the present invention from about 0.2% to about 15% by weight and preferably at about 6% by weight.

Preferably, the hollow microspheres are of a size, from about 30 to about 160 microns and most preferably about 90 microns. Hollow microspheres are used in combination with a polyester, to reduce the density of the polyester and to enhance overall performance properties of the polyester. Such performance properties include the ability to flow under shear forces involved in centrifugation and to facilitate the separation of blood serum or plasma from the cellular portion of blood when used in blood collection tubes.

The selection of hollow microspheres as density modifiers is because they are relatively inert having little interaction with blood components and therapeutic drugs and have a density of approximately one-tenth of most thermoset resins and are able to occupy about 10 times more volume than thermoset resins, reducing actual volume of separator composition. Surface modifications of the hollow microspheres can also be achieved for additional requirement of theology control of the gel formulation. Hollow microspheres are stable in polyester formulations and exhibit high strength preventing destruction during most process conditions and complexation or physical association through hydrogen bonding for example may occur between the polyesters and the spheres providing a mechanism for enhanced stability and flow thixotropy.

Alternatively, the density reducing component may be a mineral oil gel comprising a di-block and tri-block copolymer. Most preferably, the mineral oil gel has a viscosity of about 20,000 cps to about 160,000 cps, at about 25° C.

An alternate embodiment of the present invention preferably comprises, (i) about 20% to about 50% by weight of a mineral oil gel having di-block or tri-block copolymers; and (ii) about 80% to about 50% by weight of a high density polyester.

An additional component that may be used in the formulations of the present invention is a silica thickener. A silica thickener is a further density and/or theology modifier.

An additional component that may be used in the formulations of the present invention is a trimethylolpropane based polyoxyalkylene stabilizer. A polyol stabilizer is added because of its thickening ability. An additional component that may be used in the formulations of the present invention is titanium dioxide. Titanium dioxide may be added as an opacifier.

Preferably, the gel formulations of the present invention may be used in blood collection applications. Most notably, in blood collection tubes.

Referring to the drawings in which like reference characters refer to like parts throughout the several views thereof, FIG. 1 shows a typical blood collection tube 10, having an open end 16, a closed end 18 and a stopper 14 that includes a lower annular portion or skirt 15 which extends into and presses against the inside wall 12 of the tube for maintaining stopper 14 in place.

FIG. 2 shows the use of the gel formulations of the present invention in a typical blood collection tube. A gel formulation 20 is shown at the closed end of the tube.

A blood sample of interest can be transferred into tube 10 that comprises gel formulation 20. Tube 10 is then placed in a centrifuge and subjected to centrifugal force. This causes the gel formulation 20 to move to a point dividing the heavier and lighter fractions of the sample.

Measurement of both complex moduli as a function of strain indicate the strain sensitivity or deformation behavior of the gels which enable the required flow characteristics under centrifugation. The examples that follow illustrate the measurement of the complex moduli of the commercially available gel formulations and the gel formulations of the present invention.

Various other modifications will be apparent to and may be readily made by those skilled in the art without departing from the scope and spirit of the invention.

The examples are not limited to any specific embodiment of the invention, but are only exemplary.

EXAMPLE 1

PREPARATION AND ANALYSIS OF THE FORMULATIONS OF THE PRESENT INVENTION

Various sample formulations of the present invention were prepared in accordance with the weight percents shown in Table 1. Each sample formulation was prepared by mixing silica with one haft of the polyester and blended under vacuum. Following adequate dispersion, the balance of the polyester was added with the density reducing component and when chosen, a polyol stabilizer. Mixing was initiated under vacuum until well dispersed. All mixing was completed at room temperature. The density of the sample formulation was then achieved at a certain temperature. Each sample formulation is identified in Table 1.

The density of the formulations were calculated from a simple mixing role:

$$\Sigma x_i (\text{Density}_i) = \text{Gel Density}$$

where $x_i$=mole fraction Density$_i$=Component

The viscosity of the formulations were measured using a parallel plate geometry (25 mm) with a spacing of 1.2 mm and shear rate of 0.05 sec$^{-1}$ at 25° C. Due to the internal structure of the dispersions or gels used in the present invention and in the present state-of-the-art, all formulations were allowed to re-equilibrate following loading into the test geometry for a minimum of 10 minutes prior to testing.

Oscillatory rheometry methods were used to characterize the formulations. Oscillatory rheometry involves the application of sinusoidal strain as the independent variable and the resulting shear stress as the dependent variable. For purely elastic fluids, the stress and strain are in phase; a 90° phase angle occurs for purely viscous fluids. Viscoelastic fluids exhibit a phase angle dependent on the relative proportions of viscous to elastic effects. Therefore from the phase angle determined from those oscillatory measurements, the viscous and elastic modulus components are obtained. The viscous modulus is identified as G", also known as the loss modulus and the elastic or dynamic modulus is identified as G', also known as the elastic storage modulus. These moduli are typically viewed as a function of strain to determine linear and non-linear viscoelasticity regimes and as a function of frequency. Dynamic mechanical measurements showing strain dependence of the dynamic storage modules, G', and loss modules, G", were obtained at a frequency of 10 radians/second. These measurements show that the gels of the present invention are differentiated from weakly structured dispersions.

Figure 4:
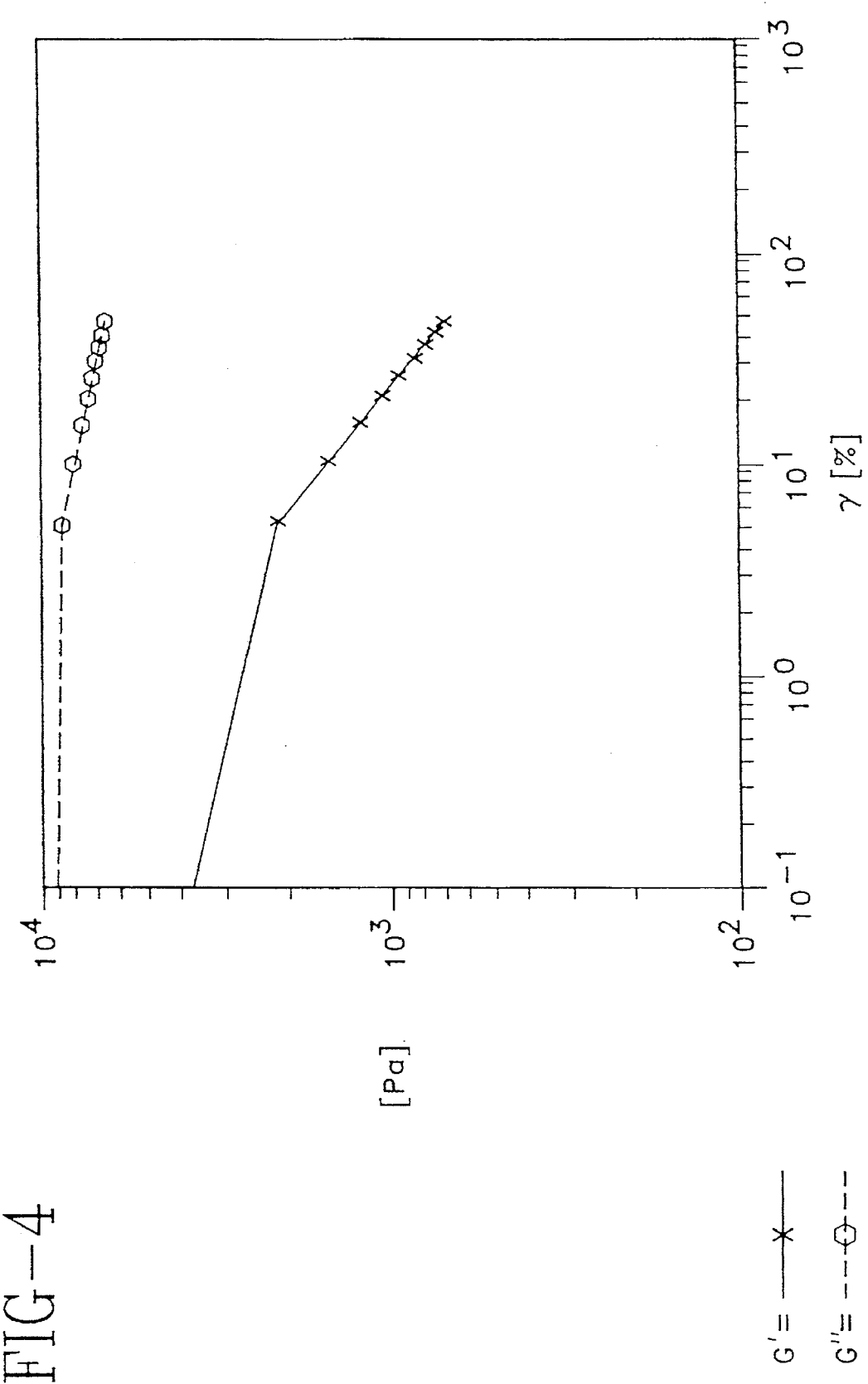
Figure 5:
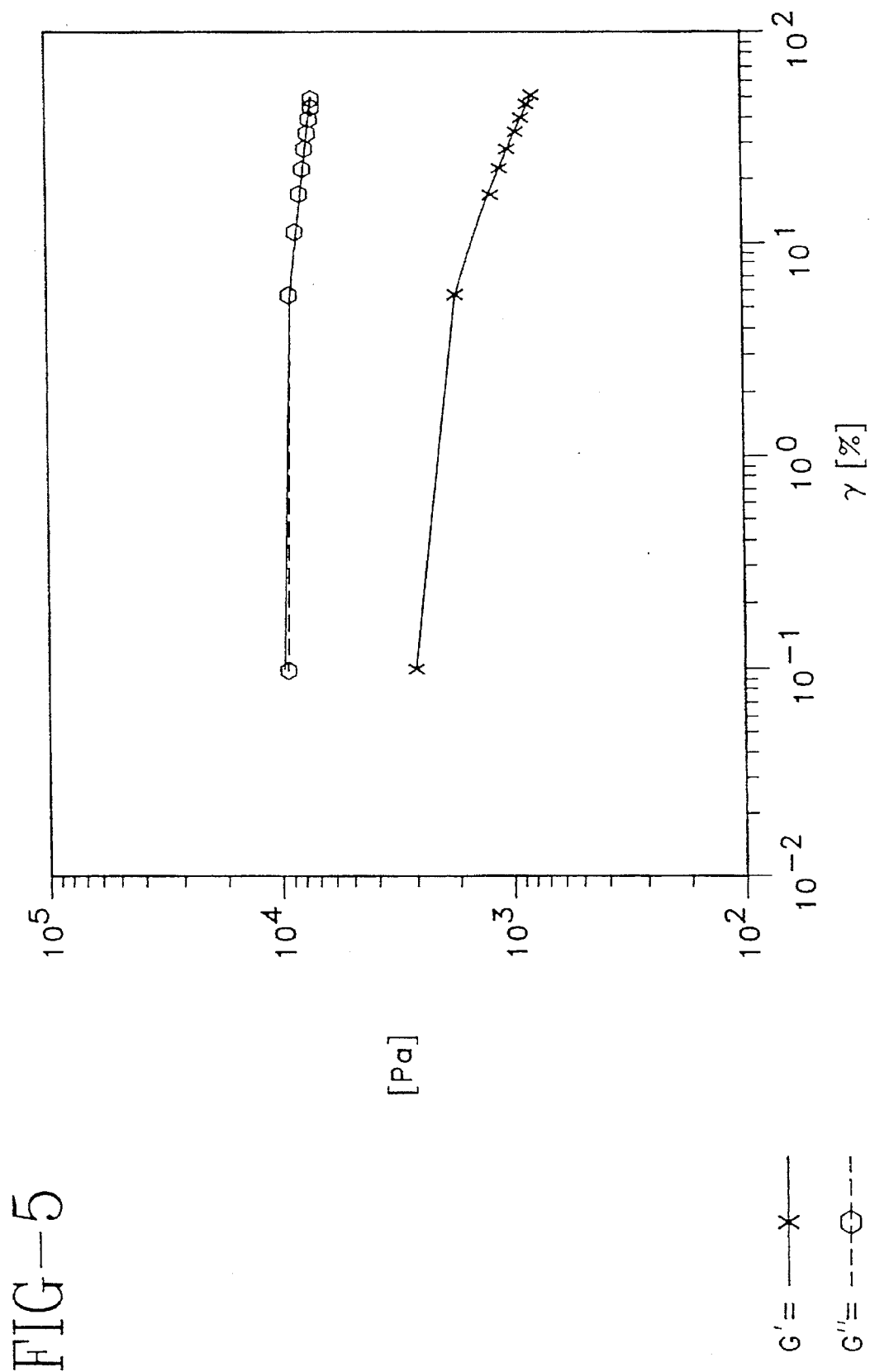
Figure 6:
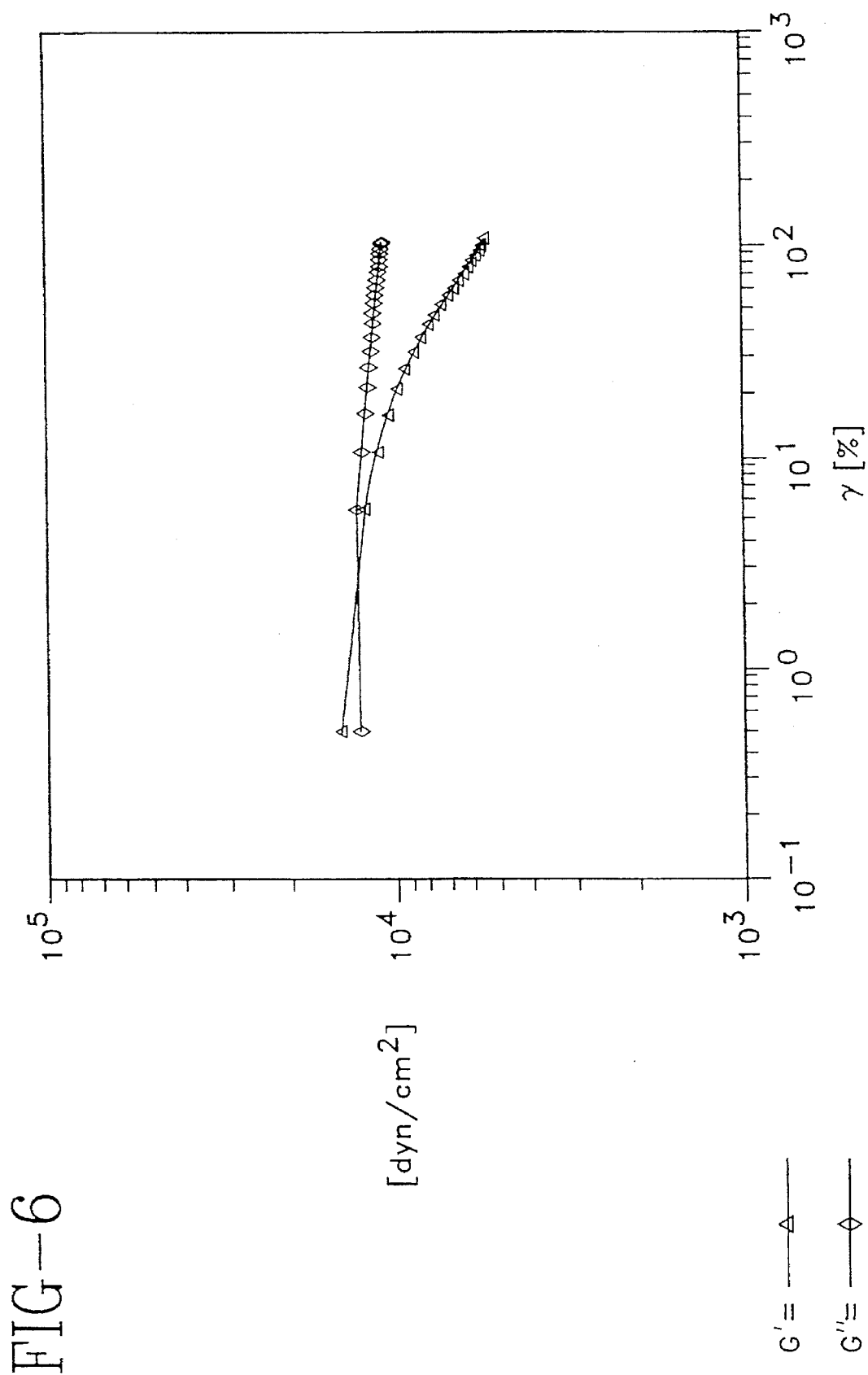
Figure 7:
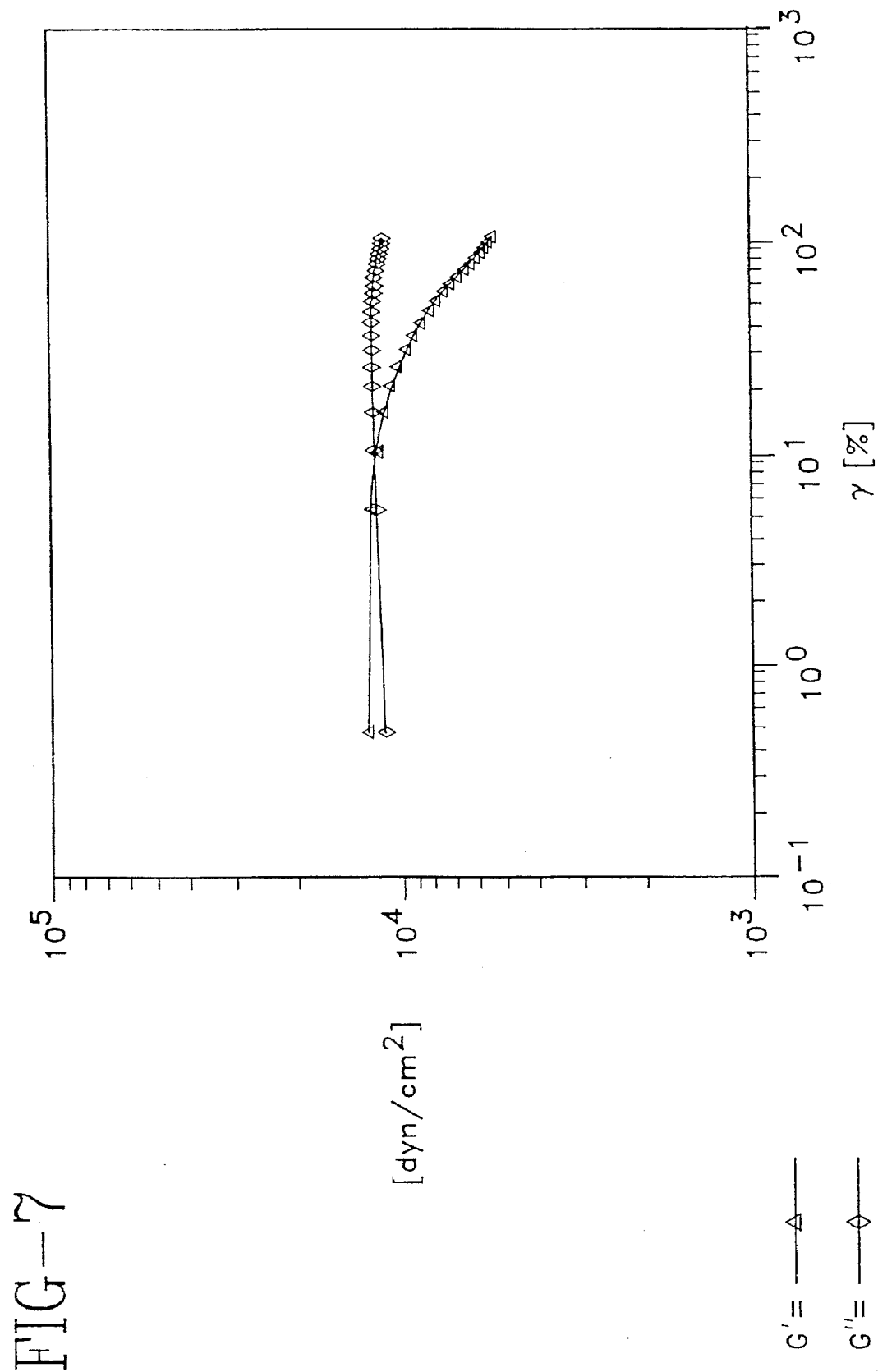
Figure 8:
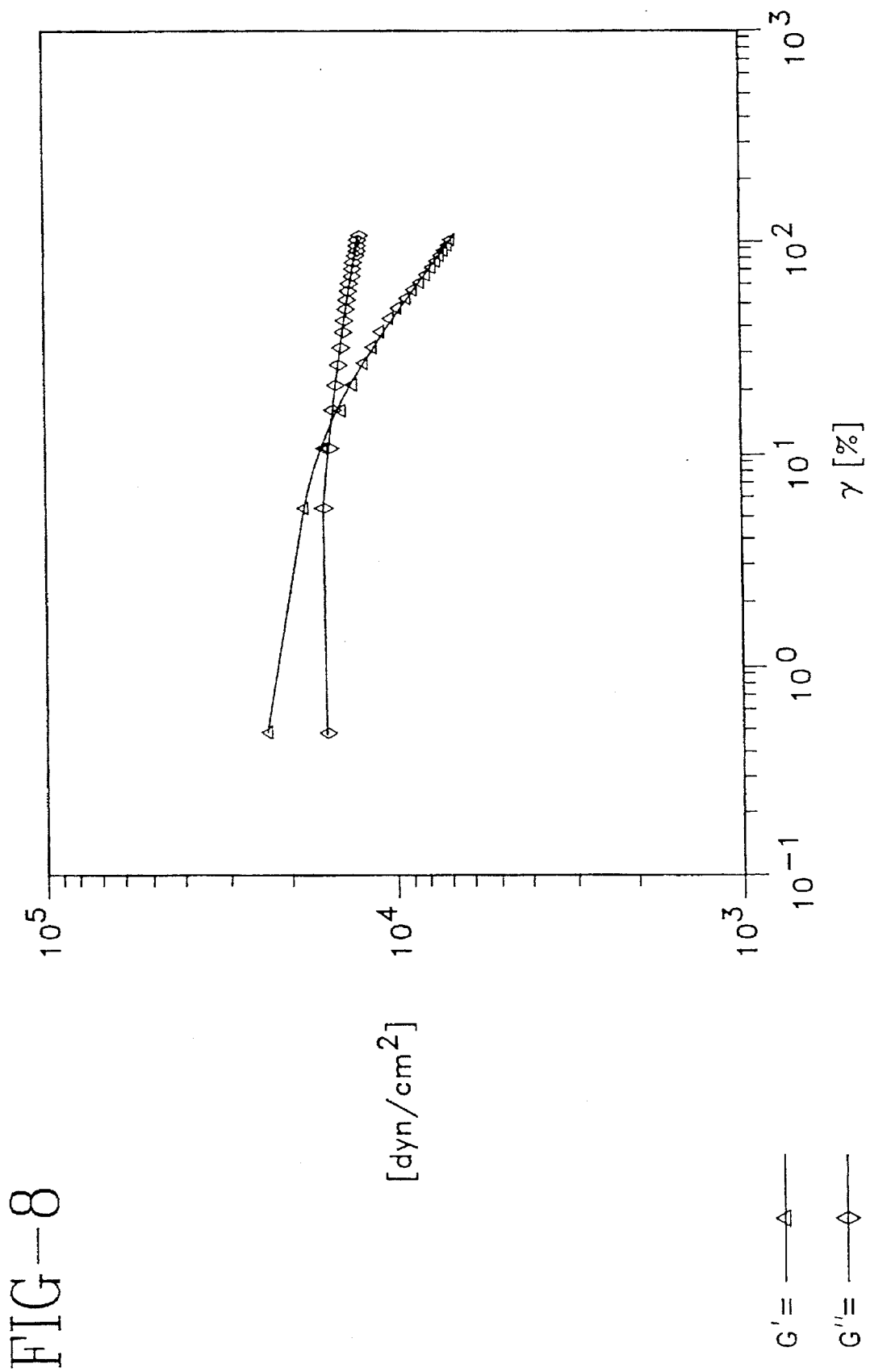

The dynamic mechanical behavior of each formulation is summarized in graphical form in FIGS. 3–10.

Commercially available serum and/or plasma separator formulations are non-linear viscoelastic dispersions and the loss modulus, G", exceeds the storage modulus, G', for formulations with strains greater than 0.005. Most notably, the formulations of the present invention are viscoelastic dispersions wherein the loss modulus G" does not exceed the storage modulus G' or where the storage modulus is greater than the loss modulus as shown in the FIGURES within the strain interval of about 0.001 to about 0.1.

TABLE 1

| | SAMPLE | | | | | | | |
|---|---|---|---|---|---|---|---|---|
| | A (wt %) | B (wt %) | C (wt %) | D (wt %) | E (wt g) | F (wt g) | G (wt g) | H (wt g) |
| ID# | 548–86 | 548–82 | 548–57 | 555–56 | 555–87 | 555–54 | 555–38 | 555–39 |
| Polyester: | | | | | | | | |
| Polyol | 94.685 | 94.68 | 93.39 | 226.0 | 232.9 | 224.6 | 277.2 | 264.0 |
| Density Reducing Component | | | | | | | | |
| Mineral Oil Gel | | | | 117.0 | 128.3 | 133.0 | 72.8 | 86.0 |
| Hollow Microspheres | 2.0 | 1.0 | 2.0 | | | | | |
| Others: | | | | | | | | |
| Polyol Stabilizer | 0.3 | 0.3 | 0.3 | | 1.1 | 1.1 | 1.1 | 1.1 |
| Hydrophobic Silica | 3.0 | 4.0 | 4.0 | 7.0 | 3.7 | | 14.6 | |
| TiO$_2$ | 0.015 | 0.015 | 0.015 | | | | .06 | .06 |
| Hydrophilic Silica | | | | | | 7.3 | | |
| Density | 1.116 | 1.04 | 1.031 | 1.0443 | 1.0441 | 1.0423 | 1.0482 | 1.0475 |
| FIG. | 3 | 4 | 5 | 6 | 7 | 8 | 9 | 10 |

What is claimed is:

1. A viscoelastic dispersion formulation comprising:
   (a) from about 85% to about 97% by weight of a high density polyol;
   (b) from about 0.2% to about 15% by weight of hollow microspheres:
   (c) from about 0.3% of a polyol stabilizer;
   (d) from about 3% to about 4% of a hydrophobic silica; and
   (e) from about 0.015% of titanium dioxide.

* * * * *